(12) United States Patent
Gilmour

(10) Patent No.: US 6,955,654 B2
(45) Date of Patent: Oct. 18, 2005

(54) RANGE OF MOTION WALKER BOOT

(75) Inventor: Robert Farrer Gilmour, Auckland (NZ)

(73) Assignee: Bodyworks Inc., Vista, CA (US)

( * ) Notice: Subject to any disclaimer, the term of this patent is extended or adjusted under 35 U.S.C. 154(b) by 0 days.

(21) Appl. No.: 10/378,897

(22) Filed: Mar. 5, 2003

(65) Prior Publication Data

US 2003/0199798 A1 Oct. 23, 2003

(30) Foreign Application Priority Data

Mar. 5, 2002 (NZ) ............................................. 517594

(51) Int. Cl.[7] .................................................. A61F 5/00
(52) U.S. Cl. ............................ 602/16; 602/23; 602/27; 128/882; 36/140; 135/84
(58) Field of Search .............................. 602/16, 23, 27, 602/28, 29, 12, 62, 65, 66; 128/108.1, 845, 123.1, 882, 892, 893; 2/22, 911, 919; 36/140; 135/84

(56) References Cited

U.S. PATENT DOCUMENTS

| | | | | | |
|---|---|---|---|---|---|
| 5,269,748 | A | * | 12/1993 | Lonardo | 602/27 |
| 5,429,588 | A | * | 7/1995 | Young et al. | 602/27 |
| 5,954,075 | A | * | 9/1999 | Gilmour | 135/84 |
| 6,024,713 | A | * | 2/2000 | Barney | 602/23 |
| 6,155,998 | A | * | 12/2000 | Gilmour | 602/27 |
| 6,361,515 | B1 | * | 3/2002 | Gilmour | 602/27 |
| 6,394,117 | B1 | * | 5/2002 | Gilmour | 135/84 |
| 6,656,145 | B1 | * | 12/2003 | Morton | 602/27 |
| 6,749,578 | B2 | * | 6/2004 | Peters | 602/27 |
| 6,764,457 | B2 | * | 7/2004 | Hogg | 602/23 |

* cited by examiner

Primary Examiner—Fadi H. Dahbour
(74) Attorney, Agent, or Firm—Young & Thompson

(57) ABSTRACT

The invention comprises a range of motion device for use between a first member and a second member, rotatable connection between the first member and the second member, a range of motion limiting elements engageable on the first member and acting on the second member to limit the range of rotational movement of the second member relative to the first member.

16 Claims, 3 Drawing Sheets

RANGE OF MOTION WALKER BOOT

TECHNICAL FIELD

This invention relates to a range of motion device and has been devised particularly, though not necessarily solely, for use with an orthopaedic walker.

BACKGROUND ART

Walkers are used as immobilisation and support structures for the lower leg and ankle. Walkers are devices for the immobilisation and protection of the lower leg, ankle and foot. Walkers typically consist of a shoe or chassis which is strapped to the patient's foot, and arms or uprights which are strapped to the lower leg. These uprights can either be fixed at 90° to the ground or there can be provision for the uprights to be fixed in a range of positions or pass through a range of permissible ankle movement. The majority of the market is for walkers with a fixed upright. A smaller percentage is for walkers providing a range of fixed positions, and/or alternatively a series of ranges of motion for the uprights.

A fixed walker has the upright set at 90° to the ground. Commonly the requirement is for a range of fixed positions between 30° of plantar flexion and 30° of dorsiflexion. Plantar flexion refers to downward movement of the foot at the ankle joint, while dorsiflexion refers to upward motion of the foot from the ankle joint.

In some clinical situations it is preferable to allow a range of motion which may be anywhere within a usual range of plus 30° (plantar flexion) to minus 30° (dorsiflexion). It is preferable to provide for settings in 5° increments.

The current art consists of a collection of metal mechanisms where stops or pins are moved to limit motion in either direction.

OBJECT OF THE INVENTION

Range of motion mechanisms, particularly for use with orthopaedic walkers, as presently available, therefore have some limitations.

It is therefore an object of the present invention to provide a range of motion device which will obviate or minimise the foregoing limitations in a simple yet effective manner or which will at least provide the public with a useful choice.

STATEMENT OF THE INVENTION

Accordingly the invention consists in a range of motion device for use between a first member and a second member, rotatable connection between the first member and the second member, a range of motion limiting means engageable on the first member and acting on the second member to limit the range of rotational movement of the second member relative to the first member.

Preferably the rotatable connection means comprises an aperture through the first member and a trunnion on the second member positionable in the aperture in the first member.

Preferably a substantially annular member surrounds the aperture and the range of motion limiting means is engageable on the substantially annular member.

Preferably the range of motion limiting means comprise a pair of further annular members each having an outward protrusion, the pair of members being engageable on the annular protrusion at selected ones of a plurality of allowable positions so that the distance between the outward protrusions can be varied so as to alter the maximum range of movement of the second member relative to the first member.

Preferably the annular protrusion has outwardly facing splines and each further annular member has inwardly facing splines engageable onto the outwardly facing splines.

Alternatively a single further annular member is provided having inward splines engageable onto the outwardly facing splines on the annular member.

Preferably the second member has a detent thereon positionable in the space between the outwardly extending protrusions.

Preferably lock means are provided to hold the first member the second member and the further annular members in engagement.

Preferably the lock means comprise a plate with a protrusion thereon and means to engage that protrusion with the trunnion.

Preferably the lock means further include a bore in, or protrusion on, the plate to engage the trunnion.

Preferably further lock means are provided to engage the plate with the first member.

Preferably the further lock means comprise slots about the annular protrusion and hook members on the plate engageable into the slots in a rotatable manner to engage the hook members with material surrounding the slots.

To those skilled in the art to which the invention relates, many changes in construction and widely differing embodiments and applications of the invention will suggest themselves without departing from the scope of the invention as defined in the appended claims. The disclosures and the description herein are purely illustrative and are not intended to be in any sense limiting.

BRIEF DESCRIPTION OF THE DRAWINGS

One preferred form of the invention will now be described with reference to the accompanying drawings in which.

BEST MODE FOR CARRYING OUT THE INVENTION

Figure 2:
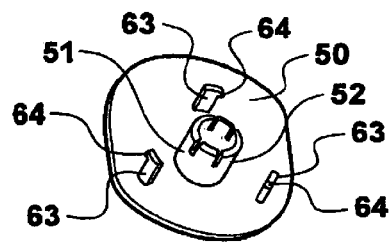
FIG. 2 is a perspective view of a plate forming part of the range of motion device shown in FIG. 1.
Figure 3:
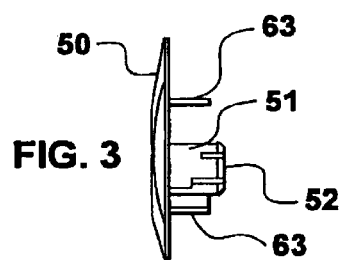
FIG. 3 is a side elevation of the plate of FIG. 2.

Referring to the drawings a range of motion device particularly to provide a control mechanism for an orthopaedic walker is provided as follows.

Figure 1:
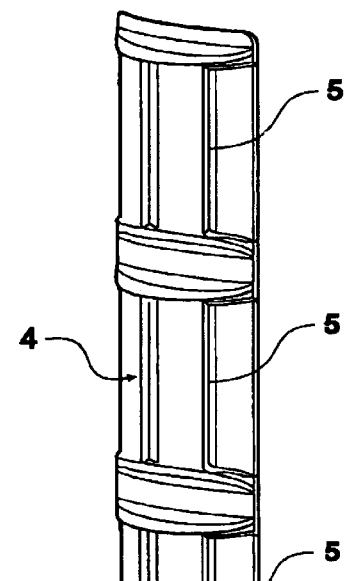
FIG. 1 is a perspective view of a walker having a range of motion device according to a preferred form of the invention shown in exploded form.
Figure 1:
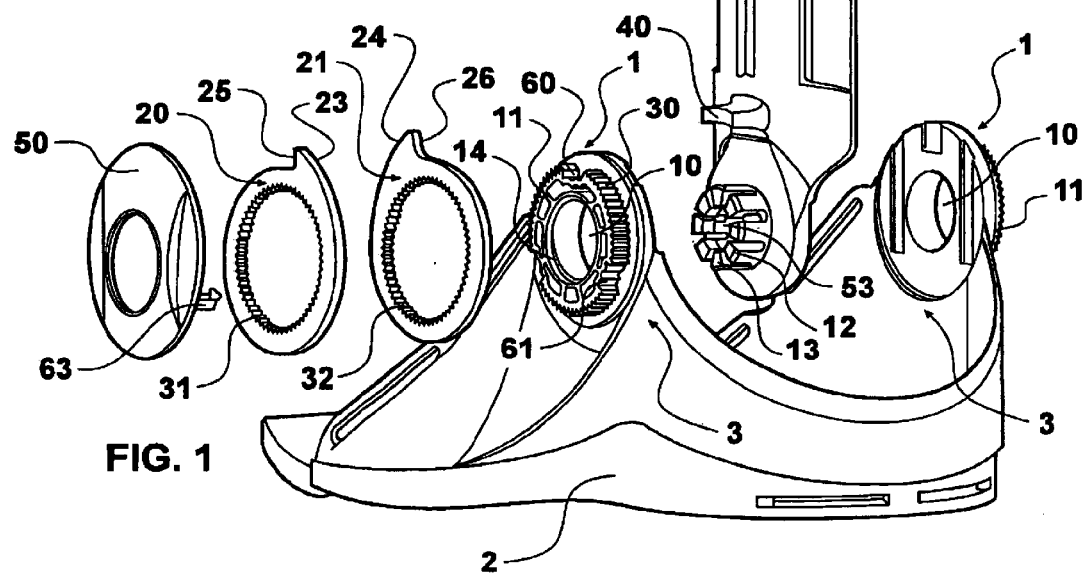

A first member 1 is provided which may comprise part of an orthopaedic walker shoe 2. As can be seen in the construction of FIG. 1 the shoe 2 has an upstanding part 3 there being one upstanding part 3 positioned to each side of the shoe. Accordingly a pair of first members 1 are provided. If desired an alternative construction which provides only a single range of motion device on the shoe can be provided.

A second member is provided which, in the preferred form, comprises an arm 4 which in use will extend up the lower leg of a user and allow the arm to be bound to the user's leg(s), for example, by passing straps or the like through apertures 5 in the arm 4.

An aperture 10 is provided in the first member and this is surrounded preferably on the outwardly facing face with an annular protrusion 11. The annular protrusion 11 can be integrally moulded with shoe 2 or could be affixed, for example, by plugging into an aperture. Such a construction has some advantages, firstly the shoe 2 is a large moulding, but protrusion 21 requires precision and making the construction in two parts aids satisfaction of these two factors. Secondly moulding in separate pieces allows different materials to be used and thirdly alternative mechanisms can be placed in the 'plug-in' aperture.

A trunnion 12 which is preferably castellated is provided on the arm 4, the trunnion being able to pass through the aperture 10 so as to be a rotatable fit therein.

If desired the ends of the arms forming the castellated trunnion may have an outwardly extending lip 13 which becomes positionable in a rebate 14 in the annular protrusion 11, for example, by being a "snap" fit therein, but still allowing the above-mentioned rotation.

Range of motion limiting means are provided to limit the rotation of the arm 4 with respect to the first member 1. In the preferred form this may take the form of a pair of further annular members 20 and 21 each of which has an outwardly extending protrusions 23 and 24 thereon. A substantially radial faces 25 and 26 is provided on the extending protrusions 23 and 24. The further annular members 20 and 21 are positionable onto the annular protrusion 11 in a manner such that a gap is formed between the outwardly extending protrusions 23 and 24 and more particularly between the radial faces 25 and 26 which are arranged to be mutually inwardly facing.

Means are provided to enable the separation of the radial faces 25 and 26 to be varied and in the preferred form this may take the form of outwardly extending splines 30 on the annular member 11 and co-operating inwardly extending splines 31 and 32 on the further annular members 20 and 21. Thus the thickness of the annular members 20 and 21 is less and preferably about half of the thickness of the annular protrusion 11. As can be seen the distance apart of the radial faces 25 and 26 can be readily varied by altering the position of engagement with the co-operating splines 30 and 31 and 30 and 32.

The arm 4 is provided with a detent 40 which extends across the first member 1 and is able, in use, to be positioned between the faces 25 and 26. If the faces 25 and 26 are positioned so that they abut the edges of the detent 40, only a relatively small range of motion of the arm 4, with respect to the first member 1, will be achieved but if the gap is larger a more substantial range of motion is provided.

Preferably the splints are arranged such that the space can be increased in 5° steps, although any suitable size of step may be provided.

To those skilled in the art to which the invention relates, many changes in construction and widely differing embodiments and applications of the invention will suggest themselves without departing from the scope of the invention as defined in the appended claims. The disclosures and the description herein are purely illustrative and are not intended to be in any sense limiting.

Lock means are provided to lock the construction together and to this end an end plate 50 is provided which has inwardly extending protrusion 51 which again may have a degree of castellation and an outwardly extending lip 52.

The protrusion 51, in use, becomes positioned within the trunnion 12 which may have a rebate at 53 over which the lip 52 is a "snap" fit. The plate is also desirably provided with a further lock means to engage the first member 1 and this may be achieved by providing a number of depressions such as 3 at 60 in the outwardly facing splined face of the annular protrusion 11 and providing slots 61 in that space. The plate 50 is provided with a number of arms 63 which are provided with a hook 64 at the ends thereof. The dimensions of the arms and hooks are such that the arm 63 and hook 64 may pass through the slots 61 allowing the plate to be rotated into its desired position in a manner such that the hooks 64 catch behind the material about the slots 61.

In order to change the range of motion the plate 50 can be rotated so that the hooks 64 become free and the plate can then be forced so that the protrusion 51 becomes free of the trunnion 12. The annular members 20 and 21 can then be moved to a new position and the construction reassembled with the range of motion of the arm 4 relative to the member 1 being varied.

A further annular member may be provided which is in effect a combination of the members 20 and 21 which will be able to be positioned on the annular protrusion 11 so as to provide a fixed range of motion. In such a construction by varying the position of the fixed single annular member the exact position over which the range of motion, if any, provided can be varied. Of course in most instances such a member would provide a zero range of motion to the arm 4.

Figure 4:
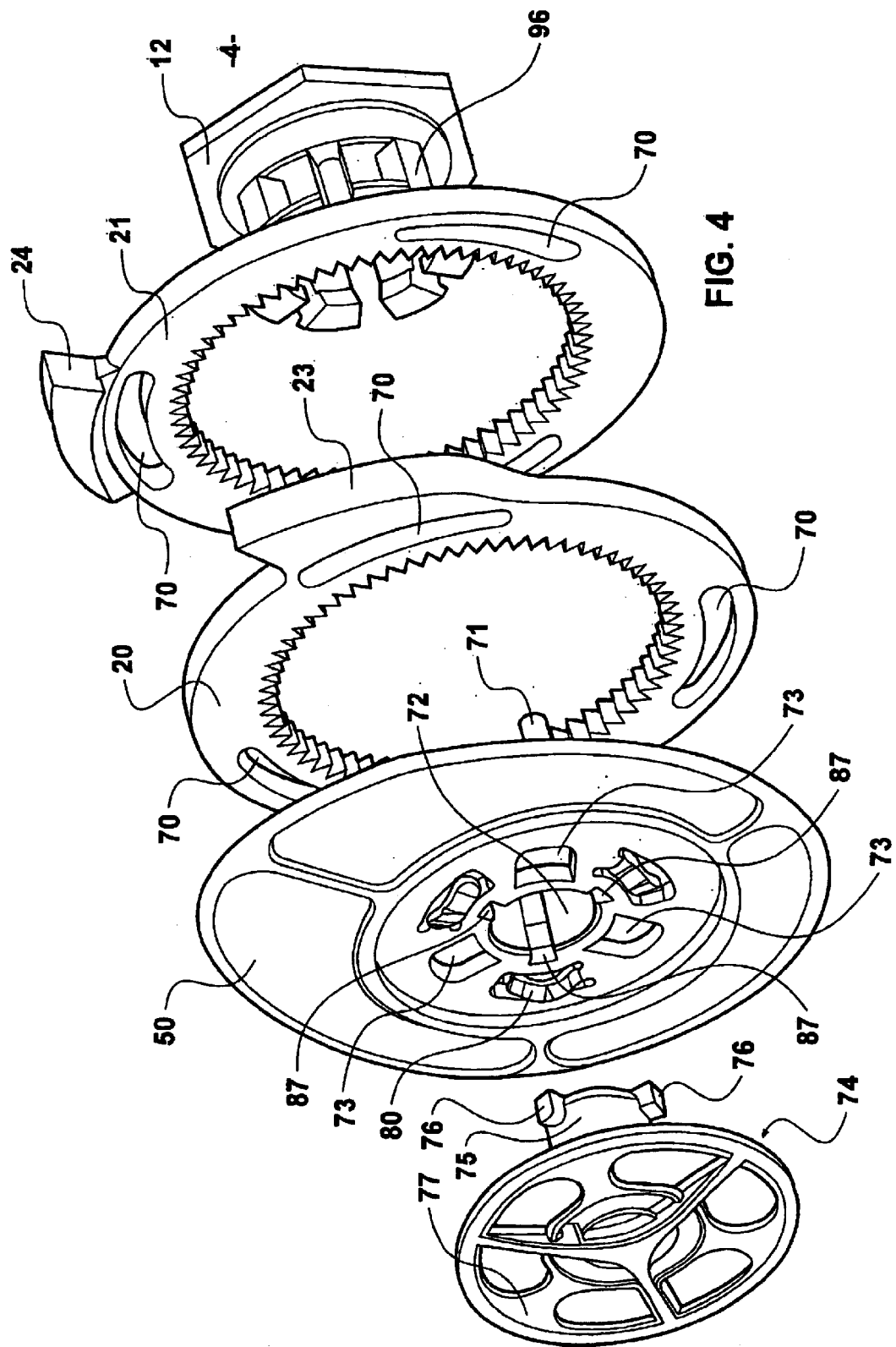
FIG. 4 is an exploded perspective view of parts of an alternative range of motion device according to the invention.
Figure 5:
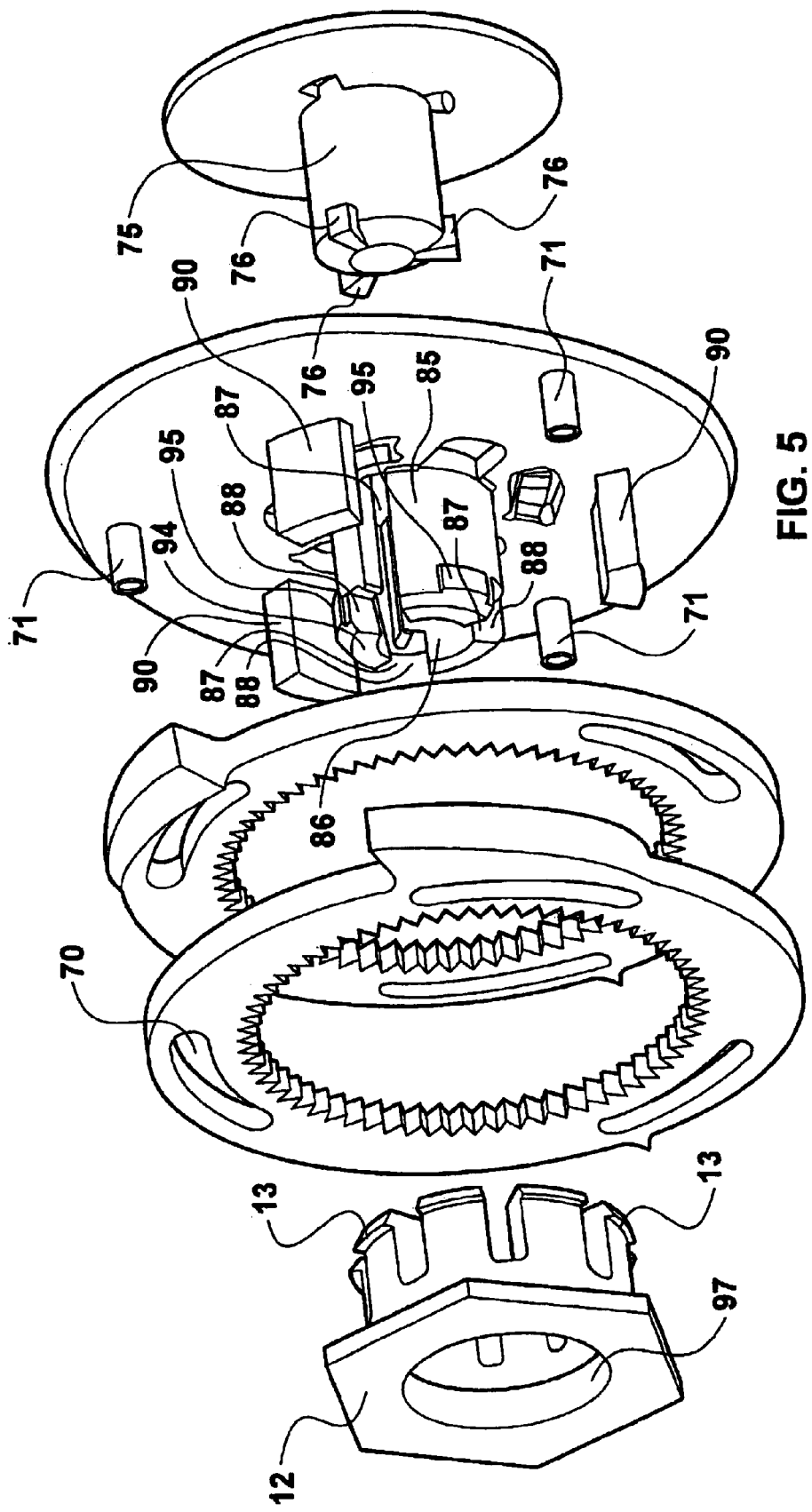
FIG. 5 is an exploded perspective view as in FIG. 4, but from the opposite hand.

Referring now to FIGS. 4 and 5, a trunnion 12 is again provided on arm 4.

Again a pair of further annual members 20 and 21 are provided although in this case further arcuate slots 70 are provided adjacent the perimeter of the annual members, Three such slots may be provided in each annual member.

In this construction the end plate 50 is replaced by a pair of plates comprising the end plate 50 and a cap member 74. The end plate 50 has inwardly extending pins 71 which are positioned in the slots 70. This restricts rotation of two annular members 20 and 21 and in particular prevents the protrusions 23 and 24 from crossing.

The end plate 50 has a central aperture 72 and apertures 73 of which, in the embodiments shown, there are three such apertures 73 spaced thereabout.

The cap member 74 has a central spigot 75 with outwardly extending lips 76 thereon substantially as for the lips 52 of the previous invention.

The spigot 75 is attached to the cap part 77. The plate 50 also has a spigot 85 with a central bore 86, The spigot 85 is provided with slots 87 therein and a rebate 88 is provided on each castellation formed by slots 87. Thus the spigot 75 passes through the apertures 72 in the end plate 50 and through the spigot 85. Once in position the end plate 50 and cap member 74 are rotated one relative to the other so that extending lips 76 enter the rebates 88. The spigot 75 causes the castellations to spread (either the spigot 75 or bore of spigot 85 may be tapered.

The end plate 50 may be also shaped to provide resilient protrusions 80 which bear upon the inner surface of the end cap member 74. The end plate 50 also is provided with tongues 90 which in use are positioned as for the previous embodiment.

The distal end 94 of spigot 85 has raised ridges 95 thereon which engage in a groove or rebate 96 in the bore of trunnion 12 to hold the construction when assembled loosely in place. When the spigot 85 is fully inserted into the bore of trunnion 12 the ridges enter a further groove 97. Pushing spigot 75 into the bore of spigot 85 causes spigot 85 to spread which and pushes the raised ridges 95 further into groove 97. The construction can be disassembled by rotation of the cap 74 relative to end plate 50 until the outwardly extending lips 76 clear the rebates 88. The resilient protrusions 80 will push the cap 74 away from the end plate 50 allowing cap 74 to be gripped and removed so that the raised ridges 95 clear the groove 97 (or at least are easily removed).

In use the range of motion device is assembled as above described and the distance between the radial faces 25 and 26 set to achieve the range of motion required by, for example, the orthopaedic surgeon.

If the need varies or the walker is passed to a different patient, by disassembling the range of motion machine the range of motion can be altered.

Thus it can be seen that at least in the preferred form of the invention a range of motion device is provided which will operate as a control mechanism particularly, though not necessarily solely, for an orthopaedic walker.

It is an advantage of the construction that in a simple manner, without the use of pins or other devices, the range of motion may be varied over a substantial range in relatively small steps which is advantageous.

What is claimed is:

1. A range of motion device for use between a first member and a second member, comprising a rotatable connection between the first member and the second member, a range of motion limiting means engageable on the first member and acting on the second member to limit the range of rotational movement of the second member relative to the first member, the range of motion limiting means comprising a pair of rotatable annular members each having an outward protrusion, the pair of rotatable members being engageable on the first member at selected ones of a plurality of allowable positions so that the distance between the outward protrusions can be varied so as to alter the maximum range of movement of the second member relative to the first member.

2. A range of motion device as claimed in claim 1, wherein the rotatable connection means comprises an aperture through the first member and a trunnion on the second member positionable in the aperture in the first member.

3. A range of motion device as claimed in claim 2 wherein a fixed substantially annular member surrounds the aperture and the rotatable members are engageable on the fixed substantially annular member.

4. A range of motion device as claimed in claim 1, wherein a fixed substantially annular member surrounds the aperture and the rotatable members are engageable on the fixed substantially annular member.

5. A range of motion device as claimed in claim 1, wherein the fixed annular member has outwardly facing splines and each rotatable annular member has inwardly facing splines engageable onto the outwardly facing splines.

6. A range of motion device as claimed in claim 5 wherein lock means are provided to hold the first member the second member and the further annular members in engagement.

7. A range of motion device as claimed in claim 6 wherein the lock means comprise a plate with a protrusion thereon and means to engage that protrusion with the trunnion.

8. A range of motion device as claimed in claim 7 wherein the lock means further include a bore in, or protrusion on, the plate to engage the trunnion.

9. A range of motion device as claimed in claim 8 wherein further lock means are provided to engage the plate with the first member.

10. A range of motion device as claimed in claim 9 wherein the further lock means comprise slots about the annular protrusion and hook members on the plate engageable into the slots in a rotatable manner to engage the hook members with material surrounding the slots.

11. A range of motion device as claimed in claim 7 wherein further lock means are provided to engage the plate with the first member.

12. A range of motion device as claimed in claim 11 wherein the further lock means comprise slots about the annular protrusion and hook members on the plate engageable into the slots in a rotatable manner to engage the hook members with material surrounding the slots.

13. A range of motion device as claimed in claim 5 wherein the second member has a detent thereon positionable in the space between the outwardly extending protrusions.

14. A range of motion device as claimed in claim 1, wherein a single further annular member is provided having inward splines engageable onto the outwardly facing splines on the annular member.

15. A range of motion device as claimed in claim 14 wherein the second member has a detent thereon positionable in the space between the outwardly extending protrusions.

16. A range of motion device as claimed in claim 1, wherein the second member has a detent thereon positionable in the space between the outwardly extending protrusions.

\* \* \* \* \*